US006809326B2

(12) United States Patent
Disabito et al.

(10) Patent No.: US 6,809,326 B2
(45) Date of Patent: Oct. 26, 2004

(54) ADJUSTABLE OZONE DELIVERY SYSTEM FOR AIR DISINFECTION

(75) Inventors: James L. Disabito, Brandon, VT (US); Mark E. Kurtz, Fort Lauderdale, FL (US); Scott P. Russell, Rutland, VT (US)

(73) Assignee: Ultravation, Inc., Brandon, VT (US)

( * ) Notice: Subject to any disclaimer, the term of this patent is extended or adjusted under 35 U.S.C. 154(b) by 0 days.

(21) Appl. No.: 10/250,928

(22) PCT Filed: Jan. 9, 2002

(86) PCT No.: PCT/US02/00575

§ 371 (c)(1),
(2), (4) Date: Jul. 7, 2003

(87) PCT Pub. No.: WO02/076512

PCT Pub. Date: Oct. 3, 2002

(65) Prior Publication Data

US 2004/0051056 A1 Mar. 18, 2004

Related U.S. Application Data

(60) Provisional application No. 60/260,565, filed on Jan. 9, 2001.

(51) Int. Cl.[7] .................................................. A61N 5/06
(52) U.S. Cl. ............................ 250/504 R; 250/455.11
(58) Field of Search ....................... 250/504 R, 455.11, 250/432 R; 422/120, 121

(56) References Cited

U.S. PATENT DOCUMENTS

| 4,922,114 A | * | 5/1990 | Boehme ..................... 250/436 |
| 4,967,090 A | | 10/1990 | Schlitt |
| 5,557,112 A | | 9/1996 | Csoknyai et al. |
| 5,601,786 A | | 2/1997 | Monagan |
| 5,742,063 A | | 4/1998 | Scroggins et al. |
| 5,751,007 A | | 5/1998 | Weaver |
| 5,817,276 A | | 10/1998 | Fencl et al. |
| 5,894,130 A | | 4/1999 | Bach |
| 5,902,552 A | * | 5/1999 | Brickley ..................... 422/121 |
| 5,925,320 A | | 7/1999 | Jones |
| 6,071,473 A | | 6/2000 | Darwin |

OTHER PUBLICATIONS

World Book Online Americas Edition, "Ultraviolet Rays," 2001, 2 pages, World Book, Inc., USA.
Encarta Encyclopedia Article Titled "Ultraviolet Radiation," Microsoft Encarta Online Encyclopedia 2000, 2000, 2 pages, Microsoft Corporation, USA.
Ge Quartz "Lamp Tubing," 1997, 1998, 1999, 5 pages, General Electric Company, USA.
Osram Sylvania "Quartz Tubing," 2000, pp. 1, 5–6, 8–13, Osram Sylvania, USA.
Steril–Aire UVC for HVAC, "Guide to UVC Emitters," Undated, 6 pages, Steril–Aire, Inc., iUSA.
Technical Data for Lexan Monolithic Sheet, Undated, 1 page, General Electric Company, USA.
Philips, "Quartz and Special Glass Factory," Undated, Sheets 1 and 3, Philips Corporation. USA.
Oxford Dictionary of Science, pp. 811–812, 1999, Market House Books, Ltd., Oxford University Press.

* cited by examiner

*Primary Examiner*—Kiet T. Nguyen
(74) *Attorney, Agent, or Firm*—Law Offices of Kenneth F. Dusyn (57) ABSTRACT

An UV light system (10) for treating the air includes an UV tube lamp (20) having a first section (42) for transmitting UV light in a wavelength range thaht includes maximum ozone production and maximum germicidal activity, and a second section (44) for transmitting UV light in a wavelength range thaht includes maximum germical activity while excluding the production of ozone; and a movable annualar sleeve (46) for controlling the amount of ozone transmitted by the lamp (20).

44 Claims, 7 Drawing Sheets

ADJUSTABLE OZONE DELIVERY SYSTEM FOR AIR DISINFECTION

This application claims priority to U.S. Provisional Patent Application Serial No. 60/260,565 filed Jan. 9, 2001.

TECHNICAL FIELD OF THE INVENTION

The present invention relates to an ultraviolet (hereinafter "UV") light apparatus, module and system for the treatment of air which, upon exposure to UV light, will destroy harmful bacteria, micro-organisms and/or offensive and noxious odors in the air contained within a confined space or in air passing through a confined space such as a conduit or a heating/ventilation air conditioning (hereinafter "HVAC") duct.

BACKGROUND ART OF THE INVENTION

UV light sources for the treatment of air typically take the form of a UV lamp positioned within a confined space such as the cross-sectional area of a conduit, for example, in a HVAC duct located in the home or an office building. UV lamps, such as those disclosed in U.S. Pat. No. 5,751,007 issued May 12, 1998, are known to emit UV light through two different types of tubing contained in the lamp, thereby generating UV light at different radiation wavelengths for destroying harmful bacteria and for the production of ozone to remove offensive and noxious odors. According to the disclosure of this patent, one kind of tubing will transmit light at wavelengths over the full radiation spectrum of UV light (what the patent refers to as UVA and UVB light), and the other tubing will transmit light at wavelengths only above 200 nanometers (defined in the patent as UVA light). The patent refers to UVA light as that light which is transmitted at wavelengths above 200 nanometers, and UVB light as that light which is transmitted at radiation wavelengths below 200 nanometers. However, according to a Microsoft Encarta Online Encyclopedia article entitled "Ultraviolet Light" by Thomas W. Davis, M.S., Ph.D. (published by the Microsoft Corporation, 2000), UV light is often divided into three different wavelength categories: UVA, UVB and UVC. In general, the shorter wavelengths of UV radiation are more dangerous to living organisms. Thus, UVA light has a wavelength from about 400 to about 315 nanometers; UVB light occurs at wavelengths from about 315 to about 280 nanometers, which causes sunburn and can cause skin cancer upon prolonged exposure; and UVC light has radiation wavelengths of approximately 290 to 15 nanometers which is often used to sterilize surfaces because of its germicidal activity against bacteria, viruses and micro-organisms. The "Oxford Dictionary Of Science," on the other hand, classifies ultraviolet light ranges according to its effects on the human skin, as UV-A (320–400 nm), UV-B (290–320), and UV-C (230–290 nm). And according to U.S. Pat. No. 4,967,090 issued Oct. 30, 1990, the U.S. FDA (Food and Drug Administration) defines UVA as the region of 320–400 nm and UVB as the region of 260–320 nm. In view of the foregoing discrepancies, and for the purposes of describing the invention herein, the term UVC shall refer to that ultraviolet light which occurs in the range of from about 15 to about 290 nanometers. Nonetheless, tubing consisting of special formula glass may be designed to be transparent to the longer UV wavelengths, while the use of pure quartz tubing is transparent to the entire, naturally occurring range of UV light, including ultraviolet ranges below 200 nm.

Within the UVC range of ultraviolet light as defined above, maximum germicidal activity is recognized to occur at a radiation wavelength of about 253.7 nanometers. As indicated above, germicidal activity alone (without the production of ozone) can be effected by the use of specially prepared quartz tubing for the UV lamp that is commonly referred to in the industry as L-quartz, which is quartz doped with titanium dioxide. However, when UVC light interacts with the oxygen in the ambient atmosphere at a radiation wavelength of approximately 185 nanometers, maximum ozone generation and output occurs. The production of ozone at this wavelength helps to reduce or substantially eliminate offensive and/or noxious odors that occur within the air, such as in air conditioning ducts in the home or office buildings when no fresh air is being introduced into the system. This condition generally occurs when air is being constantly re-circulated through a HVAC system under circumstances when minimal amounts of fresh air are introduced into the system, typically during cold weather conditions in order to conserve heat and reduce energy consumption.

As indicated above, ozone production from a UV lamp can be effected by the use of high quality clear quartz tubing, available and referred to in the industry as VH-quartz, which allows the transmission of UV light at both the 185 and 253.7 nanometer radiation wavelengths. Therefore, by employing a UV lamp having both these types of tubing, in combination with an adjustable sleeve covering a portion of the VH-quartz tubing for blocking or absorbing the transmission of ultraviolet light that will produce ozone, such as that described in U.S. Pat. No. 5,751,007, one can purify and/or treat the air and simultaneously control the production of ozone for eliminating offensive and/or noxious odors.

Unfortunately, the control of the rate of ozone emitted in a HVAC duct by a system that employs the UV lamp apparatus described in U.S. Pat. No. 5,751,007, is hampered by the duct system that conveys the conditioned air, either because of the inaccessibility of the UV lamp itself, or because of the necessity of having to shut down the UV air disinfection system to manually adjust the sleeve which, in this patent, is mounted directly to the lamp's tubing. It is therefore important and desirable to monitor the levels of ozone and provide for the manual and/or automatic adjustment of the sleeve from a location exterior and/or remote from the duct system, without having to shut down the operation of the UV air disinfection system. Discontinuing operation of the system to either change the lamp or to manually adjust the sleeve's position for controlling the UV lamp's ozone output also leads to an inefficient operation. Furthermore, it should be kept in mind that while the formation of ozone within the duct is desirable for reducing and/or eliminating noxious odors, the ozone produced should not reach levels where it becomes toxic to the persons being exposed to it, since prolonged exposure to elevated levels of ozone can be harmful.

BRIEF DISCLOSURE OF THE INVENTION

In order to overcome the foregoing difficulties, the present invention provides an ultraviolet light apparatus, module and system for the treatment of air within a confined structure, such as a HVAC duct, to disinfect the air therein, and for controlling the amount of ozone generated by the ultraviolet light apparatus for substantially reducing and/or eliminating offensive and/or noxious odors carried by the air within the confined structure.

The ultraviolet light apparatus comprises an ultraviolet light-emitting lamp that includes at least one composite tubing which comprises (a) a first section for transmitting ultraviolet light in a wavelength range that includes maximum ozone production and maximum germicidal activity; and (b) a second section for transmitting ultraviolet light in a wavelength range that includes maximum germicidal activity and excludes the production of ozone. The ultraviolet light apparatus also includes (c) a movable annular sleeve whose annulus completely surrounds a portion of the composite tubing of the ultraviolet light-emitting lamp in a frictionless manner. The sleeve is capable of blocking ultraviolet light in a wavelength range that produces ozone while simultaneously allowing the transmission of ultraviolet light at a wavelength range that produces germicidal activity.

The ultraviolet light-emitting lamp may be configured as comprising a straight composite tubing, or it may comprise two, substantially parallel, tubularly connected segments, the first section of the composite tubing forming a portion of at least one of the segments. This includes a UV lamp having a generally C-shaped configuration whose opposite ends terminate in a common lamp base.

The annular sleeve is such that it is capable of blocking ultraviolet light in a wavelength range that produces ozone while simultaneously allowing the transmission of ultraviolet light in a wavelength range that produces germicidal activity. In order to accomplish this, the sleeve is preferably constructed of specially prepared fused quartz (known in the industry as "L-quartz") or transparent Teflon®. The annular sleeve is preferably of sufficient length to completely surround the first section of the composite tubing of the ultraviolet light-emitting lamp.

Alternatively, the entire tubing of the ultraviolet light-emitting lamp may be such that it will transmit ultraviolet light in a wavelength range that includes maximum ozone production and maximum germicidal activity, and includes tubing that has a straight length as well as two, substantially parallel, tubularly connected segments as described above. In either case, the opening of the sleeve combined with the sleeve's length, is configured such that it will completely surround the entire tubing of the ultraviolet light-emitting lamp. The annular sleeve has the same characteristics as the sleeve described above for the UV lamp comprising the composite tubing.

The invention also extends to the utilization of the ultraviolet light apparatus in modular form for operation of the annular sleeve to control the amount of ozone transmitted by the ultraviolet light-emitting apparatus to a confined space, e.g., a conduit having the passage of air flowing therethrough. Therefore, in addition to the ultraviolet light apparatus, the ultraviolet light module comprises a drive mechanism for the frictionless displacement of the annular sleeve along the longitudinal axis of the ultraviolet light apparatus' composite tubing for controlling the amount of ozone transmitted by the same.

In one aspect of the invention, the drive mechanism comprises an elongate threaded rod engaged at one end portion thereof with a means for rotating the rod, preferably an electric motor, with the opposite end portion of the rod being operatively engaged with a correspondingly threaded opening within a retainer member mounted to or fixed to the annular sleeve. When the threaded rod is rotated by, for example, an electric motor, or manually by the employment of a handle on the end portion of the threaded rod, the annular sleeve will be displaced along the longitudinal axis of the composite tubing of the ultraviolet light-emitting lamp. A guide rod may optionally be detachably fixed to the conduit to which the module is incorporated with, such that the guide rod communicates with a slidable stabilizer member fixed to the retainer member, the guide rod being in parallel relationship with the threaded rod to prevent the transmission of torsional forces to the annular sleeve by the rotation of the threaded rod.

Alternatively, and in keeping with another aspect of the invention, the drive mechanism may comprise a pneumatically or hydraulically operated piston secured about one end of an elongate rod, with the retainer member being secured about the opposite end of the elongate rod for the displacement of annular sleeve along the longitudinal axis of the composite tubing of the lamp when the piston is activated.

In yet another aspect of the invention, the ultraviolet light module may additionally comprise a housing for the drive mechanism, preferably configured so that the housing, ultraviolet light apparatus, and drive mechanism form a single unit. The housing, in turn, may also include a ballast for powering the ultraviolet light apparatus as well as a socket means mounted to or integral with the housing for receiving the ultraviolet lamp. A switch means may optionally be included with the housing for automatically disconnecting electrical power to the ultraviolet light-emitting lamp and/or drive mechanism when the housing is separated from the confined space, e.g., a conduit for the passage of air therethrough to which the ultraviolet light module is incorporated. In addition, the housing may also include an electrically activated, audible and/or visual alarm when the ultraviolet light-emitting lamp, ballast or drive mechanism ceases to function.

As an ultraviolet light air treatment system, the housing, ultraviolet light apparatus and drive mechanism are configured to form a single unit for incorporation with a conduit for treating the air passing therethrough.

BRIEF DESCRIPTION OF THE DRAWINGS

A complete understanding of the present invention may be obtained by reference to the following specification when taken in conjunction with the accompanying drawings wherein certain preferred embodiments are illustrated and wherein like numerals refer to like parts throughout.

DETAILED DESCRIPTION OF THE INVENTION AND BEST MODES THEREOF

An understanding of the present invention may be obtained by reference to the following description when taken in conjunction with the accompanying drawings wherein certain preferred embodiments are illustrated and wherein like numerals refer to like parts throughout.

Figure 1:
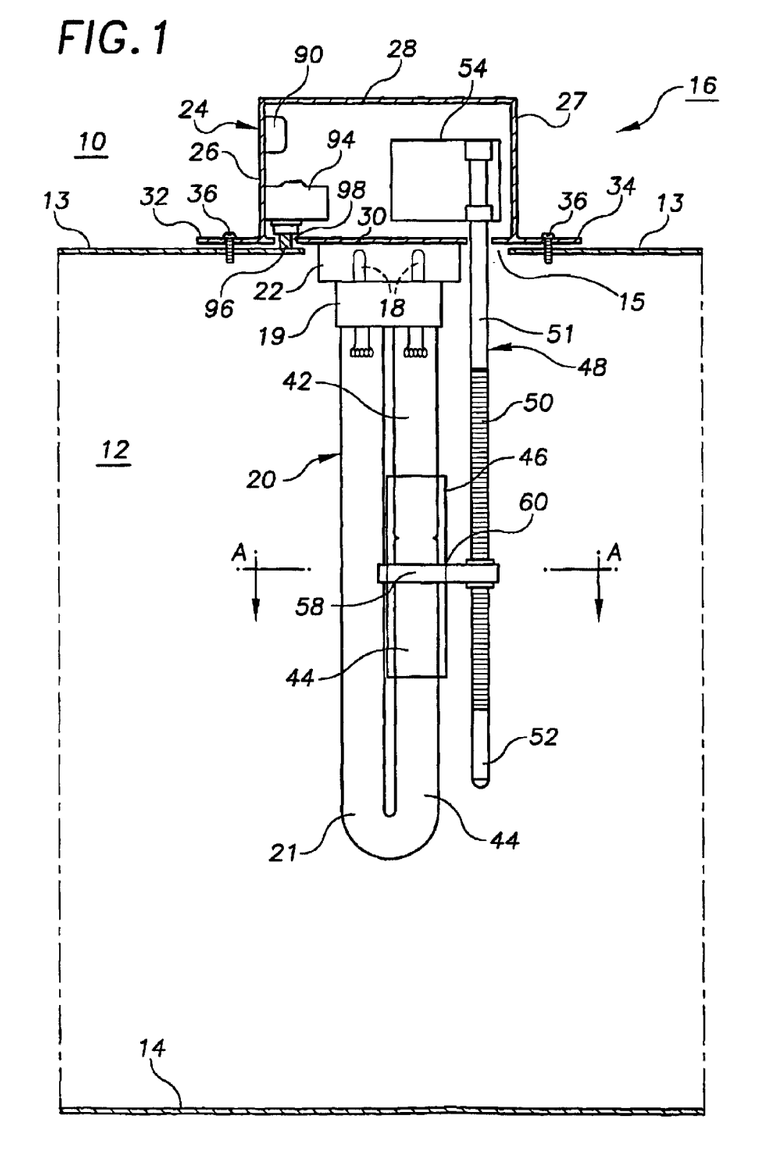
FIG. 1 is an elevated plan view of an ultraviolet light air purification system in accordance with the present invention.

Referring to FIG. 1, a UV light air purification system 10 is illustrated which includes an air duct 12 having a generally rectangular cross-section defined in part by sidewalls 13 and 14 for the passage of air therethrough. A duct opening 15 is provided in sidewall 13 for the incorporation of an ultraviolet light module 16 for the treatment of air within air duct 12. In the illustrations shown in FIGS. 1, 5 and 6, module 16 comprises a rectangularly shaped housing 24 having a hollow interior defined by sidewalls 26 and 27, top wall 28 and platform 30. Platform 30 extends beyond sidewalls 26 and 27 of housing 24 in a lateral direction parallel to sidewall 13 of air duct 12 to form respective flanges 32 and 34 for the insertion of threaded screws 36, or similar fasteners, therethrough into duct sidewall 13. This has the effect of securing housing 24, and hence module 16, to air duct 12.

As shown in FIG. 1, a lamp socket 22 is secured to the underside of platform 30 of housing 24 to receive electrical pins 18 of at least one UV lamp 20. When coupled with socket 22, UV lamp 20 will extend from platform 30 in a substantially perpendicular direction. As a result, UV lamp 20 will be disposed transversely to the flow of air in air duct 12 when the lamp is inserted through duct opening 15 and the housing 24 secured to duct wall 13. In the illustrations shown in FIGS. 1 and 5, UV lamp 20 has two pins, although more than two are contemplated depending on the configuration of the UV lamp used, e.g., four-pin lamps 20 illustrated in FIGS. 6 and 8. In FIGS. 1, 5, 6, and 8, UV lamp 20 is configured in a U-shaped arrangement whereby both ends of U-shaped tube 21 are mounted to a lamp base such as end cap 19. Tube 21, however, need not be restricted to a U-shaped configuration, and according to the invention, may be configured as a straight length of tubing (see FIG. 9) or any other shape adapted for insertion into a conduit containing the passage of air therethrough. For example, UV lamp 20 can be configured as two parallel sections of tubing connected to each other about the end opposite to its common base, by a cross-section of tubing such as that illustrated in FIG. 3 of U.S. Pat. No. 5,902,552.

Figure 7:
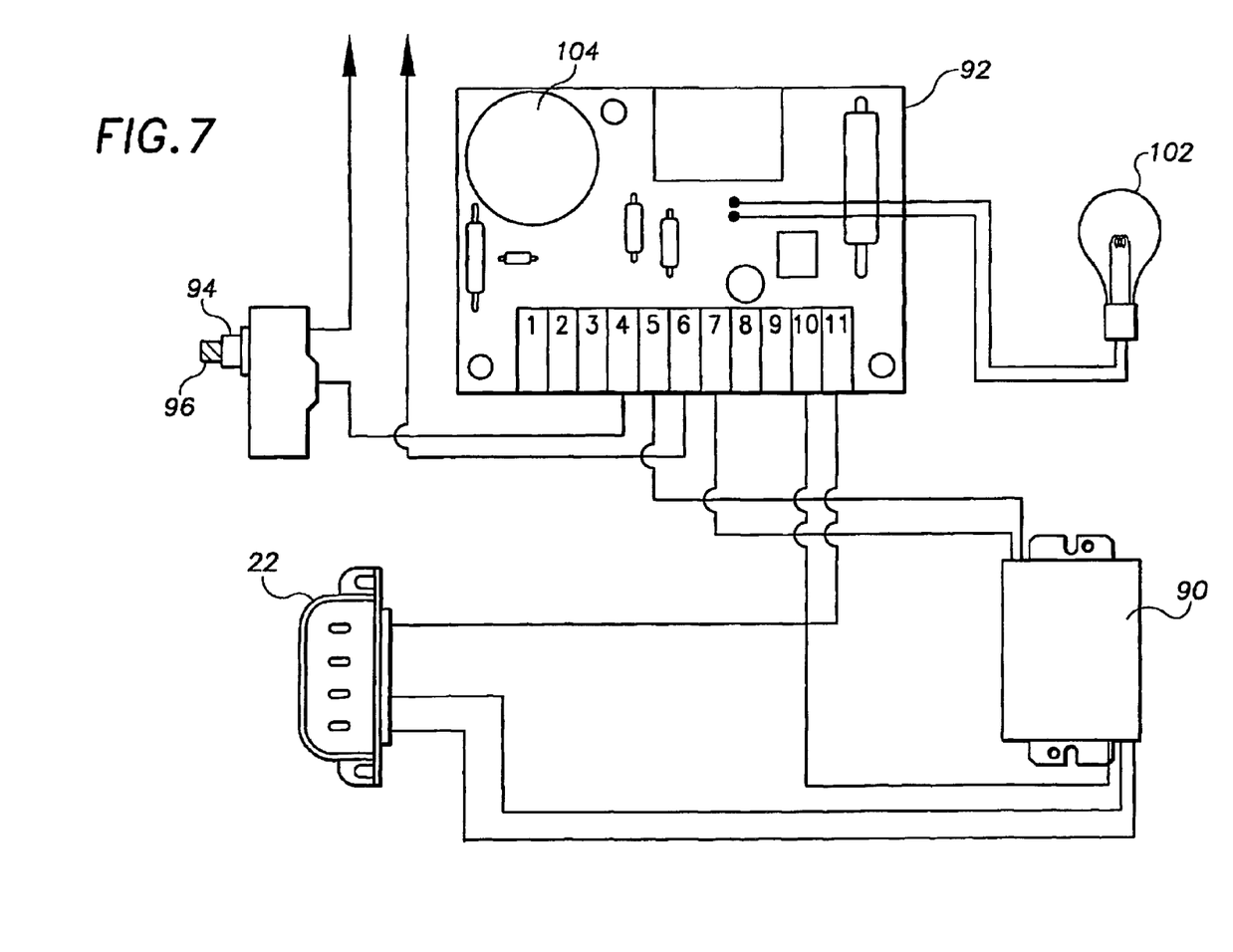
FIG. 7 is a schematic diagram illustrating the electrical connection between the UV lamp socket 22 and interlock switch 94, illustrated in FIG. 1, with ballast 90.

The electrical pins 18 provided in end cap 19 are inserted into a lamp socket 22 mounted to or integral with platform 30, which in turn is electrically connected to a ballast 90 located within housing 24 for supplying electrical power to UV lamp 20 (see also FIG. 7). It will be understood that the electrical ballast can be omitted from housing 24 of module 16 when it is convenient or desirable to locate the ballast(s) in a remote location, e.g., with a source of electrical power for electrically activating module 16.

Figure 5:
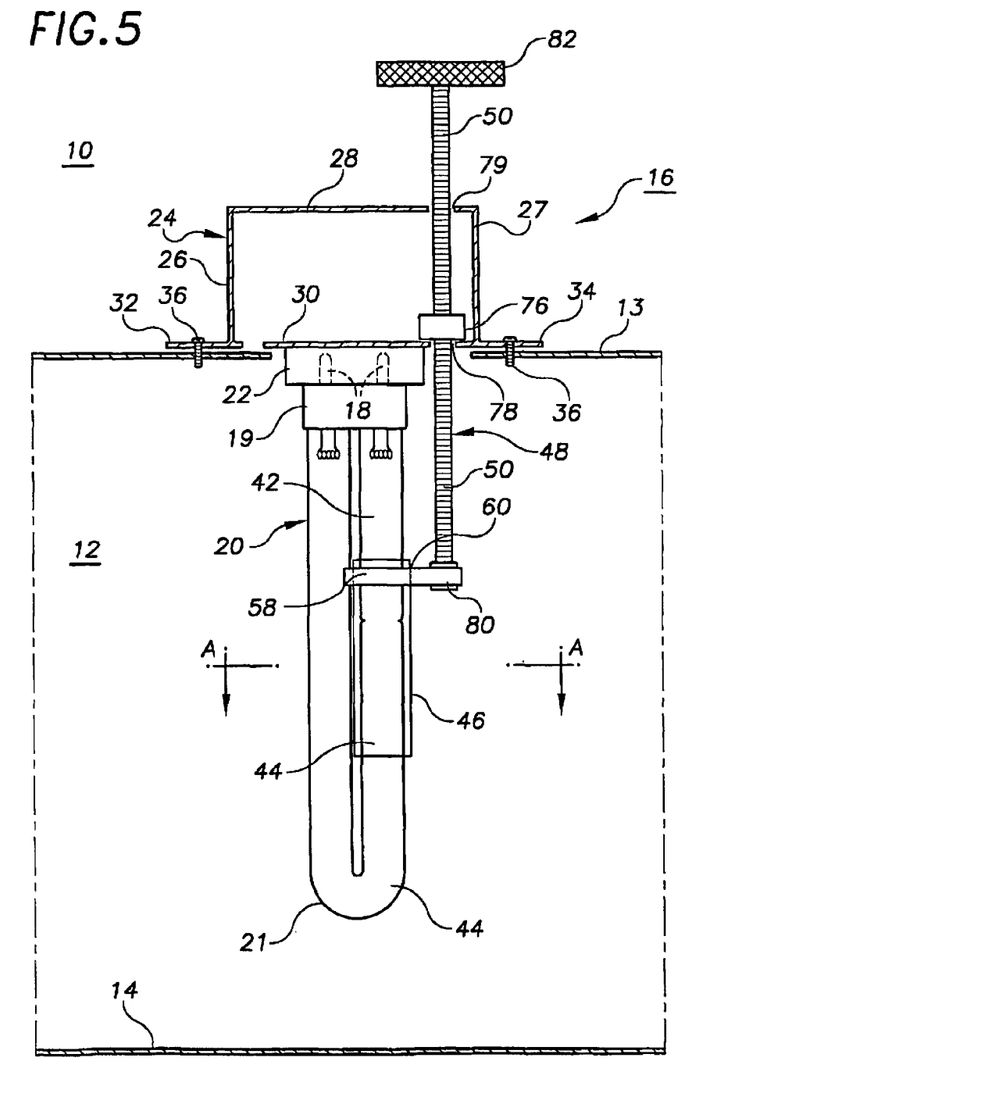
FIG. 5 is an elevated plan view of the ultraviolet light air purification system illustrated in FIG. 1 showing another embodiment for the drive mechanism 48 in accordance with the invention.
Figure 6:
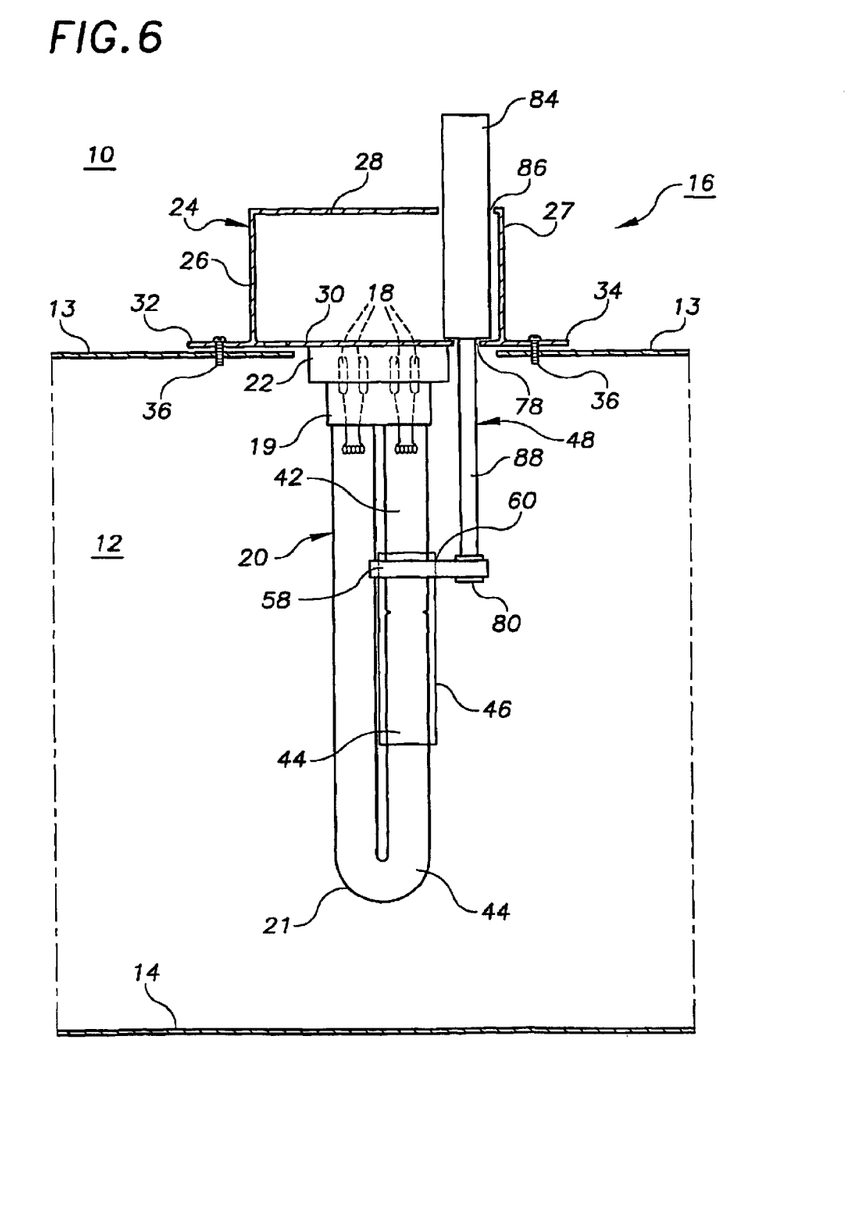
FIG. 6 is an elevated plan view of the ultraviolet light air purification system illustrated in FIG. 1 showing yet another embodiment for the drive mechanism 48 in accordance with the invention.

With regard to the UV lamp 20 shown in FIG. 1, one of the straight portions of U-shaped tube 21 has two sections of glass tubing, tubing 42 and tubing 44, joined together end-to-end to form a composite. The composite tubing has a cylindrical shape to provide a continuous lamp structure. Tubing 42, which is the shorter length illustrated in FIGS. 1, 5 and 6, is of the type that permits transmission of ultraviolet radiation within the UVC range of light as defined herein, and necessarily includes the wavelength for maximum ozone output of about 185 nanometers and the wavelength that generates maximum germicidal activity at about 253.7 nanometers. Tubing 42, therefore, allows the transmission of ultraviolet light at radiation wavelengths that will generate a maximum amount of ozone when exposed to the air, and also at wavelengths for maximum germicidal activity. Tubing 42 is generally constructed of high quality clear quartz, typically known as VH-quartz which is available from the General Electric Company under the product designation GE Quartz, Type 214, or from the Phillips Corporation under the product designation PH300/308. The GE Quartz, Type 214 VH-quartz tubing will transmit UVC light at wavelengths in the 15 to 280 nanometer range.

In the embodiments illustrated in FIGS. 1, 5 and 6, tubing 44 has a longer length and extends to and includes the opposite parallel portion of U-shaped tube 21. Tubing 44 is also of the type that will permit radiation of ultraviolet light within the UVC range but will block the transmission of deep, high energy wavelengths that cause ozone generation, e.g., wavelengths below about 200 nanometers. Tubing 44 will therefore allow the generation of ultraviolet light at wavelengths that permit germicidal activity, including maximum germicidal activity at about 253.7 nanometers, while simultaneously blocking the transmission of ultraviolet light necessary for the production of ozone, inclusive of the radiation wavelength of 185 nm. This type of glass or fused quartz is commonly referred to in the industry as L-quartz (which is quartz doped with titanium dioxide) and is available from the General Electric Company under the product designation GE Quartz, Type 219, or from the Phillips Corporation under the product designation PH304.

The ozone output of UV lamp 20 may be varied and therefore controlled by the generally coaxial movement of an annular sleeve 46 mounted in a frictionless manner about the partial length of the composite tubing formed by tubings 42 and 44. Annular sleeve 46 is sized to permit its annular opening to be coaxially disposed about tubings 42 and 44 so that the sleeve can be moved along the axial length of the composite tubing in a frictionless manner. It will be understood that in the lamp configurations illustrated in FIGS. 1, 5 and 6, UV lamp 20 is prefabricated with annular sleeve 46 mounted in place. Annular sleeve 46 is made of a transparent substance that is capable of blocking the UV wavelength of light for producing ozone while simultaneously permitting the transmission of ultraviolet wavelength of light for generating germicidal activity, including maximum germicidal activity at a wavelength of about 253.7 nanometers. It will be appreciated that the fused quartz or transparent Teflon® described below for annular sleeve 46 will not entirely block the ultraviolet radiation wavelength that generates ozone, e.g., as will a metal tube, but will block a very substantial portion of the ultraviolet radiation that generates ozone. Thus, only a very minor and insignificant amount of ozone may be generated when sleeve 46 totally surrounds tubing 42. Accordingly, the term "block" or "blocking" as used herein is meant to describe the ability to substantially impede the transmission of ultraviolet light in a range that produces ozone.

Annular sleeve 46, which in FIGS. 1, 5 and 6 has a length equal to or greater than tubing 42, may be constructed of fused quartz, such as L-quartz, or transparent Teflon®. The length of annular sleeve 46 is such that it will substantially surround tubing 42 to block the transmission of ozone to the degree desired. If maximum blockage is desired, then the length of annular sleeve 46 will be equal to or greater, preferably greater, than that portion of tubing 42 which generates the transmission of ozone.

By utilizing a transparent annular sleeve with the foregoing qualifications and attributes, as opposed to a sleeve constructed of a non-transparent substance, e.g., a material such as that described in U.S. Pat. No. 5,751,007 which utilizes metal which entirely blocks all ultraviolet light, or a transparent substance that absorbs the transmission of ultraviolet light such as polycarbonate, a more efficient UV light apparatus, module and air purification system is provided. For example, when annular sleeve 46 partially or fully covers tubing 42 of UV lamp 20, UV light is still transmitted through tubing 42 and annular sleeve 46 which includes the wavelength having maximum germicidal activity, thereby offering a greater exposure of UV light to the air passing through air duct 12.

In accordance with the invention, the UV light air purification system and module also includes a drive mechanism 48 operably communicating with annular sleeve 46 for the upward and downward displacement of the sleeve along the longitudinal axis of composite tubings 42 and 44 for varying the ozone output of UV lamp 20. This arrangement, which is illustrated in FIGS. 1, 5 and 6, avoids mounting of the sleeve directly to the lamp tubing as undertaken in the disclosure of U.S. Pat. No. 5,751,007.

Referring to FIG. 1, one embodiment for the drive mechanism 48 includes an elongate threaded rod 50 having a threadless end portion 51 operatively engaged with an electric motor 54 located within housing 24 for turning threaded rod 50 in a clockwise and counter-clockwise manner. As shown in greater detail in FIG. 2, threaded rod 50 is engaged with a correspondingly threaded opening 56 provided within sleeve retainer 58. A correspondingly threaded nut 57 overlies threaded opening 56 and is fixed to sleeve retainer 58 to accommodate the receipt and proper alignment of threaded rod 50 with the sleeve retainer. The opposite lower end 52 of rod 50 is threadless to limit the downward displacement of annular sleeve 46 relative to tubings 42 and 44. The end of sleeve retainer 58 opposite to its threaded opening 56 is provided with a circular opening 60 configured for receiving and retaining sleeve 46 therein by any conventional means, for example, by a resistance fit through the employment of a resilient annular ring, e.g., an O-ring (not shown), secured about the circumference of opening 60.

Figure 2:
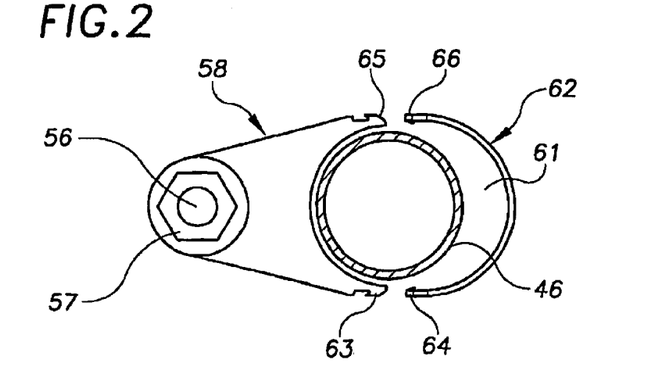
FIG. 2 is an isolated top plan view of an exploded sleeve retainer member 58 for mounting with the annular sleeve 46 illustrated in FIG. 1.

FIG. 2 illustrates another embodiment of sleeve retainer 58 according to the invention. The opposite, lateral portion of sleeve retainer 58 is configured in a semicircular fashion for engaging approximately one half of the circumference of annular sleeve 46, the remaining circumference of the sleeve being embraced by a semicircular resilient clip 62 for containing annular sleeve 46 within the circular opening 61 defined by the joinder of sleeve retainer 58 with resilient clip 62. A pair of respectively mateable notches 63,65 and 64,66 is provided about the respective ends of sleeve retainer 58 and resilient clip 62 for securing annular sleeve 46 to sleeve retainer 58.

Figure 3:
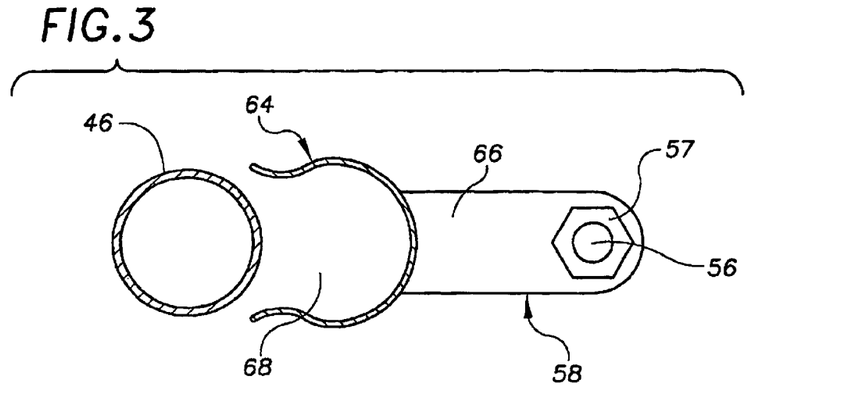
FIG. 3 is an isolated top plan view of another embodiment of a sleeve retainer member 64 for connection with the annular sleeve 46 illustrated in FIG. 1.

Yet another arrangement for fixing annular sleeve 46 to sleeve retainer 58 is illustrated in FIG. 3 wherein a circular portion of a "broom" clip 64 is secured about the end 66 of sleeve retainer 58, e.g., by welding, opposite the threaded opening 56 for receiving threaded rod 50. "Broom" clip 64 is resilient in makeup and has an opening 68 for securely receiving and retaining annular sleeve 46 therein. In this manner, "broom" clip 64 can be pushed onto annular sleeve 46 to hold the sleeve firmly in place with sleeve retainer 58.

Figure 4:
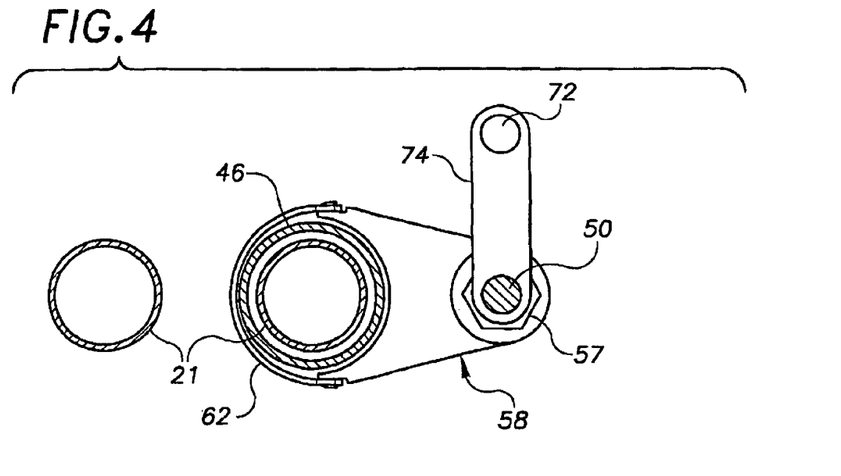
FIG. 4 is a top plan view of the UV lamp 20 taken along line A—A of FIG. 1, showing another embodiment for the assembly of sleeve retainer member 58 with annular sleeve 46 and a support arm stabilizer member 74.

As shown in FIG. 4, an elongate guide rod 70, deployed through an opening 72 within a support arm stabilizer member 74 coupled with sleeve retainer 58 via threaded rod 50, may be optionally utilized to prevent the transfer of any torsional forces to annular sleeve 46 when threaded rod 50 is rotated within the threaded opening 56 of sleeve retainer 58. Guide rod 70 is secured to sidewalls 5 and 6 (not shown) by any conventional means, and the opening 72 through which it passes is of sufficient size to permit support arm stabilizer 74 to move freely along the length of guide rod 70.

The drive mechanism of module 16, according to the invention, may also be manually operated without the necessity of using electric motor 54. For example, as shown in FIG. 5, at least one threaded nut 76 may be positioned and fixed within (or without) housing 24, the nut axially coinciding with openings 78 and 79 to receive threaded rod 50 therethrough. The lower end portion of rod 50 is threadless and coupled with an open ended receptacle 80 retained within sleeve retainer 58. The end portion of threaded rod 50 is configured to have a narrower diameter for slidable engagement with receptacle 80 (not shown) to permit its free rotation within the receptacle. Receptacle 80 may be held in place about the narrowed end portion of rod 50 by any conventional means, such as, for example, by the employment of a retainer clip or snap ring. The top portion of threaded rod 50 is provided with a handle 82 for manually turning the rod in a clockwise or counter-clockwise fashion to adjust the positioning of annular sleeve 46 about tubing 42. In this manner, the amount of ozone emitted from UV lamp 20 can be adjusted according to the needs demanded by the ambient surroundings within air duct 12 and the environment to which the air is being conducted.

As an alternative to the use of threaded rod 50 for the upward and downward displacement of annular sleeve 46, the movement of annular sleeve 46 along the axial length of tubing 42 may be accomplished by a pneumatically or hydraulically operated piston and rod combination. Referring to FIG. 6, a piston 84, whose pneumatic or hydraulic operation is conventionally known, is vertically disposed within housing 24 with the top portion thereof projecting through opening 86 provided in top wall 28. Extension rod 88 is fixed with and depends from piston 84, the opposite end of which is coupled with sleeve retainer 58 in much the same manner illustrated in FIG. 5. The lower end portion of extension rod 88 is threadless and coupled with an open ended receptacle 80 retained within sleeve retainer 58. The end portion of extension rod 88 is configured to have a narrower diameter for slidable engagement with receptacle 80 (not shown). Receptacle 80 may be held in place about the narrowed end portion of extension rod 88 by any conventional means, such as, for example, by means of a retainer clip or snap ring. The advantage of using a piston/rod combination for the vertical displacement of annular sleeve 46 in FIG. 6 is that any torsional forces that may be encountered by annular sleeve 46 through the use of threaded rod 50 in the embodiment shown in FIG. 1, are avoided. It will be understood that in accordance with the invention, any conventional drive mechanism means can be used to displace annular sleeve 46.

In order to facilitate the operation of module 16, housing 24 will preferably incorporate the electronics schematically illustrated in FIG. 7. As shown in FIGS. 1 and 7, the operation of UV lamp 20 is powered by ballast 90. Electrical motor 54, also retained within housing 24, is electrically connected to circuit board 92 which in turn receives its power from an electrical source preferably located exteriorly of housing 24 (not shown). When power is supplied to circuit board 92, and in turn to ballast 90, electric motor 54 and to an interlock switch 94 (described below), tubing 42 of UV lamp 20 will produce ultraviolet light in a radiation wavelength range within the full UVC radiation spectrum, inclusive of the 185 nanometer (i.e., below 200 nanometers) and 254.3 nanometer wavelengths for generating maximum ozone and germicidal output, respectively. Tubing 44 of UV lamp 20 will transmit UV light in a radiation wavelength range that produces germicidal activity, inclusive of the 254.3 nanometer wavelength. When it is desired to attenuate or reduce the amount of ozone being produced by module 16, electric motor 54 will be activated by an appropriate switch (not shown) operably connected to circuit board 92, to rotate threaded rod 50 in a clockwise direction. Annular sleeve 46, which is constructed of L-quartz or Teflon®, will then be displaced in the upward direction to partially cover tubing 42, thereby blocking a proportionate amount of ozone producing ultraviolet light, and hence the amount of ozone, emitted from UV lamp 20. As electrical motor 54 continues to rotate in a clockwise fashion, annular sleeve 46 will continue in the upward direction until tubing 42 is completely enveloped, thereby blocking the radiation wavelength of UV light for producing ozone. It will be noted, however, that the UV light wavelengths above those for producing ozone (generally above 200 nm), including the 253.7 nanometer wavelength for maximum germicidal activity, will continue to pass through annular sleeve 46. This has the net effect of not decreasing the amount of germicidal activity generated by UV lamp 20 even though the lamp is no longer producing ozone.

In similar fashion, when electrical motor 54 reverses the rotation of threaded rod 12 in a counter clockwise direction, annular sleeve 46 will move in a downward direction to expose tubing 42 and thereby allow controlling amounts of ozone to be introduced into air duct 12 by module 16. By displacing annular sleeve 46 in a manner to expose more or less of tubing 42, the amount of ozone produced by module 16 can be controlled from a location remote from the interior of air duct 12. Moreover, by moving annular sleeve 46 over the lower radiation wavelength tubing 42, the amount of lower radiation wavelength UV light transmitted for the production of ozone can be either blocked or attenuated without affecting the transmission of the higher radiation wavelength UV light emitted from the lower and higher radiation wavelength tubing 44. Not only is the lamp's germicidal activity increased, the ozone levels produced by the lamp can be controlled without disassembly of the duct, shutting down the system, or movement or replacement of UV lamp 20.

Figure 8:
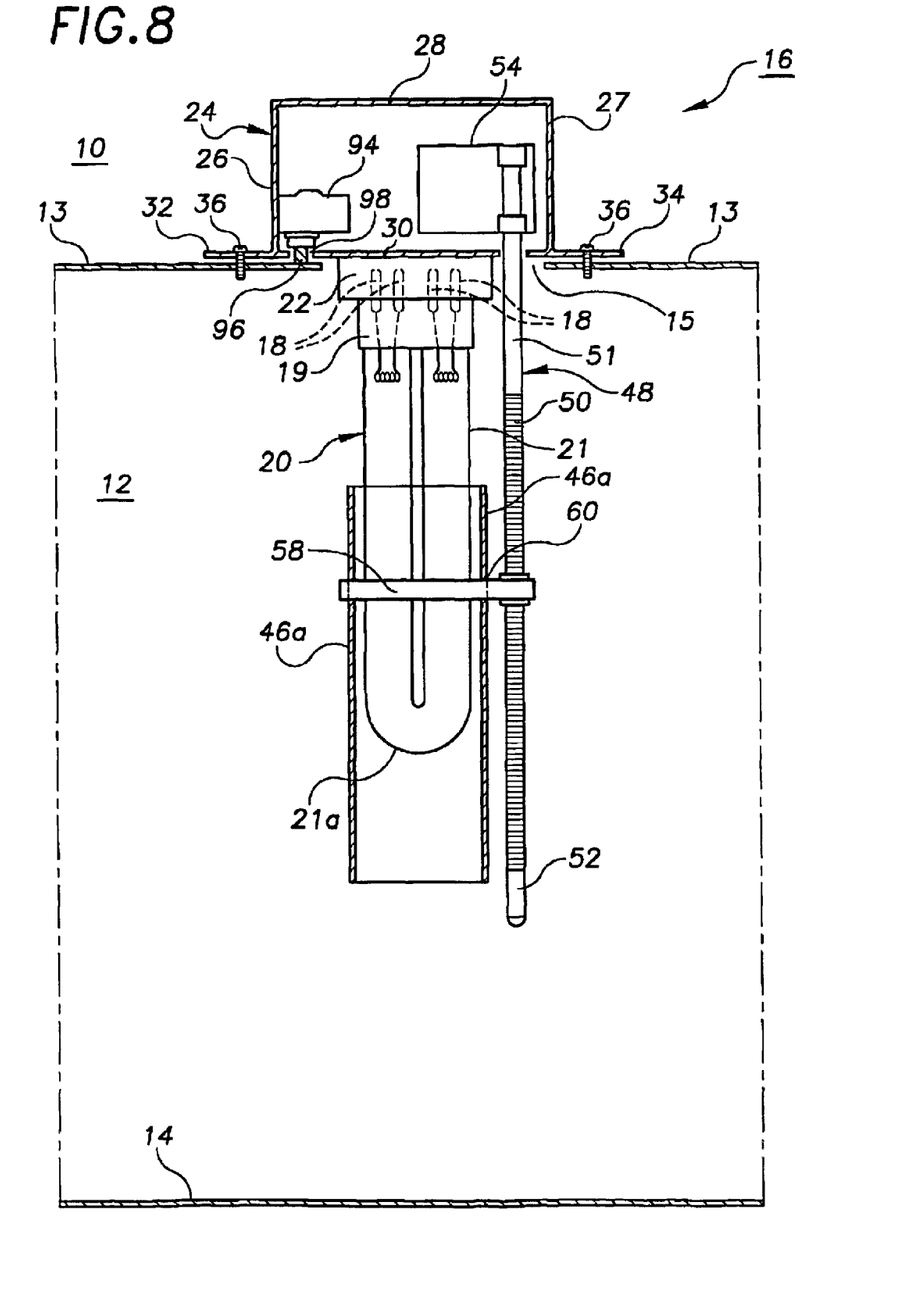
FIG. 8 is an elevated plan view of an another embodiment of the ultraviolet light air purification system illustrated in FIG. 1.
Figure 9:
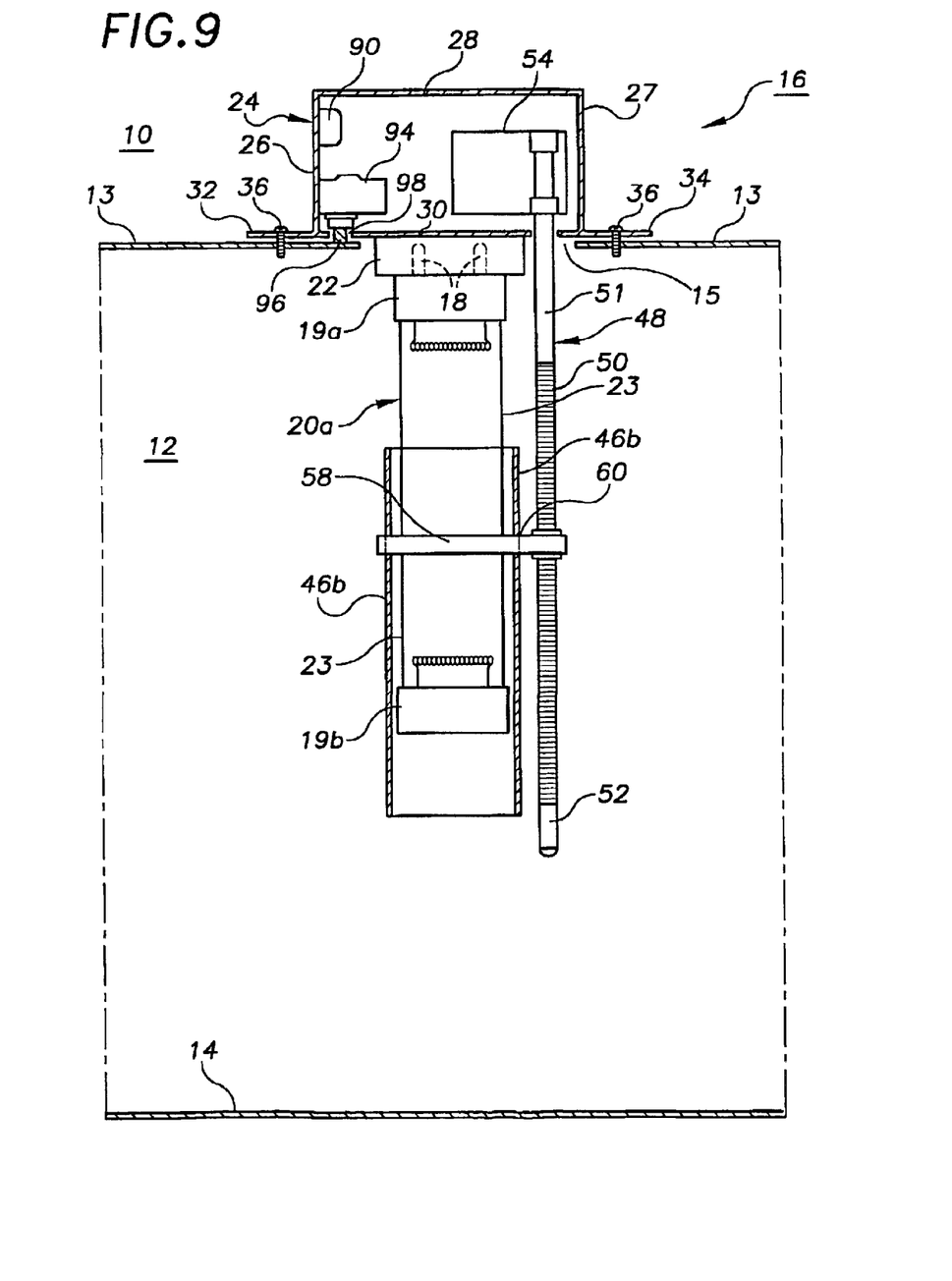
FIG. 9 is an elevated plan view of yet another embodiment of the ultraviolet light air purification system illustrated in FIG. 1.

The ultraviolet light apparatus of the invention includes other embodiments, for example, that which is illustrated in FIGS. 8 and 9. Referring to FIG. 8, in place of the composite tubing formed by tubings 42 and 44 in the embodiments illustrated in FIGS. 1, 5 and 6, the entire U-shaped tube 21 of UV lamp 20 may be configured of pure quartz, e.g., VH-quartz, that permits the transmission of ultraviolet light within the UVC range for the generation of both ozone and germicidal activity, inclusive of the 185 and 253.7 nanometer wavelengths. In this circumstance, annular sleeve 46a in FIG. 8 will be of a length and configuration to completely surround U-shaped tube 21. Therefore, when it is desired to treat the air flowing through air duct 12 without ozone, annular sleeve 46a will be movably displaced about U-shaped tube 21 to prevent or control the generation of ozone while still allowing the transmission of ultraviolet light to the air in air duct 12 for generating germicidal activity. The displacement of annular sleeve 46a along the length of U-shaped tube 21 utilizing any of the drive mechanisms described hereinbefore, enables the production of ozone to be blocked or controlled. The advantage of this aspect of the invention is that the need for composite tubing in the UV lamp is dispensed with.

It will be understood that while annular sleeve 46 describes a cylindrical configuration in FIGS. 1, 5, 6 and 9, sleeve 46a in FIG. 8 has a configuration whose opening is slightly larger than and approximates the cross-sectional area of U-shaped tube 21. It will also be understood that while it is preferred that the opening within annular sleeve 46a be slightly larger than the cross-sectional area of the tubing or lamp which it surrounds, it does not exclude other geometric constructs that will promote and economize the efficient control of ozone production from a corresponding UV lamp. In addition, provided that a greater degree of control for the generation of ozone is desired, annular sleeve 46a may be closed at the bottom thereof (not shown) to provide a "test tube" type configuration for the sleeve in order to prevent the generation of ozone from the rounded bottom portion 21a of U-shaped tubing 21.

In place of U-shaped tubing 21 illustrated in FIG. 8, the tubing of UV lamp 20 may have a straight cylindrical length as designated by the reference numeral 23 in FIG. 9. As with the U-shaped tubing 21 shown in FIG. 8, straight tubing 23 of UV lamp 20a is constructed of pure quartz, e.g., VH-quartz, that permits the transmission of ultraviolet light within the UVC range for the generation of both ozone and germicidal activity, inclusive of the 185 and 253.7 nanometer wavelengths. UV lamp 20a is provided with end caps 19a, 19b mounted at the respective ends of tubing 23 for receiving electrical wires (not shown) from their respective filaments. As is well known in the art, the electrical wires which lead from the bottom lamp filament and emanate from end cap 19b (not shown) are extended along the outside of tubing 23 for ultimate connection to ballast 90 within housing 24, generally via an extra pair of electrical pins provided in end cap 19a which would render UV lamp 20a a four-pin lamp. At the opposite end of tubing 23, end cap 19a is provided with a pair of electrical pins 18 to make electrical contact with corresponding lamp socket 22 which in turn is mounted to or integral with platform 30 of housing 24. Thus, when the end cap 19 of UV lamp 20 is plugged into lamp socket 22, the lamp will extend from platform 30 into the interior of air duct 12 as housing 24 is secured to the sidewall 13 of the air duct with threaded screws 36.

Annular sleeve 46b is of a cylindrical length to completely surround tubing 23 in a frictionless manner. Like sleeve 46 in FIGS. 1, 5 and 6 and sleeve 46a in FIG. 8, annular sleeve 46b is such that it is capable of blocking ultraviolet light in a wavelength range that produces ozone while simultaneously allowing the transmission of ultraviolet light in a wavelength range that produces germicidal activity. Annular sleeve 46b, as well as sleeve 46a, is preferably constructed of L-quartz or transparent Teflon®.

When it is desired to generate maximum ozone output from UV lamp 20a, annular sleeve 46b in FIG. 9 will be downwardly displaced to the fullest extent allowed by threaded rod 50 of drive mechanism 48 to fully expose the length of straight tubing 23 that transmits ultraviolet light within the UVC range. In order to prevent or control the generation of ozone, drive mechanism 48 is activated to displace annular sleeve 46 in the upward direction for fully or partially covering straight tubing 23.

The UV air disinfection system according to the invention may employ optional devices to facilitate the functioning of the system. For example, FIGS. 1, 8 and 9 show an interlock switch 94 secured within housing 24 for automatically disconnecting power to the ultraviolet lamp when housing 24 is removed or lifted from side wall 13 of air duct 12. The interlock switch (which may also be disposed outside of housing 24) includes a spring biased push button 96 extending through an opening 98 provided in platform 30. When housing 24 is placed over opening 15 in side wall 13 for insertion of UV lamp 20 into duct 12, push button 96 will be depressed as it comes into contact with and rests upon side wall 5, and through appropriate wiring to circuit board 92 illustrated in FIG. 7, the power to UV lamp 20 will be automatically turned on. The automatic disconnection of power to UV lamp 20 when module 16 is removed from air duct 12 will prevent inadvertent exposure to the harmful effects of the ultraviolet light emanating from UV lamp 20.

In addition to the interlock switch 94, the UV light air purification system 10 may also include an ozone detection apparatus comprising an ozone level sensor (not shown) inserted into the air passageway of duct 12 for monitoring the ozone levels produced by UV lamp 20. The ozone level sensor, which is interfaced with circuit board 92, will provide adequate notice of high levels of ozone by electronically activating a visual alarm, such as the LED indicator light 102 shown in FIG. 7. The ozone detection apparatus may also be used to automatically adjust the ozone output to preset levels by programming a microprocessor interfaced with circuit board 92 with instructions for activating electric motor 54 or piston 84 to adjust annular sleeve 46 according to the preset levels of ozone output.

The UV air purification system may also include an electrically operated audible alarm 104 and/or visual alarm, such as the LED indicator light 102 shown in FIG. 7, incorporated with (or as an adjunct to) circuit board 92 for activation in the event UV lamp 20 or the drive mechanism malfunctions, e.g., if the lamp burns out or short circuits, or if electric motor 54 or piston 84 ceases to provide movement to annular sleeve 46.

The system, module, apparatus and methods according to the invention herein provide an inexpensive and economical means by which the production of ozone within a confined structure, such as a HVAC duct, can be remotely controlled without disturbing other system components and apparatus, and without affecting and/or impeding the germicidal activity of the UV lamp.

What is claimed is:

1. An ultraviolet light module for the treatment of air within a confined space comprising:
    (a) an ultraviolet light apparatus comprising an ultraviolet light-emitting lamp that includes at least one composite tubing, said composite tubing comprising:
        (i) a first section for transmitting ultraviolet light in a wavelength range that includes maximum ozone production and maximum germicidal activity, and
        (ii) a second section for transmitting ultraviolet light in a wavelength range that includes maximum germicidal activity and excludes the production of ozone; and
        (iii) an annular sleeve, the annulus of said sleeve
            (A) completely surrounding a portion of the composite tubing of said lamp; and
            (B) being capable of blocking ultraviolet light in a wavelength range that produces ozone while simultaneously allowing the transmission of ultraviolet light in a wavelength range that produces germicidal activity; and
    (b) a drive mechanism for the frictionless displacement of said annular sleeve along the longitudinal axis of said composite tubing for controlling the amount of ozone transmitted by said ultraviolet light apparatus.

2. The module according to claim 1 wherein said lamp comprises two, substantially parallel, tubularly connected segments, the first section of said composite tubing forming a portion of at least one of said segments.

3. The module according to claim 1 wherein said sleeve allows the transmission of ultraviolet light that is inclusive of the wavelength range for producing maximum germicidal activity.

4. The module according to claim 1 wherein said sleeve has a cylindrical configuration and is of sufficient length to completely surround the first section of the composite tubing of said lamp.

5. The module according to claim 1 wherein said sleeve is constructed of fused quartz.

6. The module according to claim 1 wherein said sleeve is constructed of transparent Teflon.

7. The module according to claim 1 wherein said drive mechanism comprises an elongate threaded rod engaged at one end portion thereof with a means for rotating said rod, the opposite end portion of said rod being operatively engaged with a correspondingly threaded opening within a retainer member fixed to said sleeve for displacing said sleeve along the longitudinal axis of the composite tubing of said lamp when said rod is rotated.

8. The module according to claim 7 wherein said means for rotating said rod comprises an electric motor.

9. The module according to claim 7 wherein said means for rotating said rod comprises a handle for the manual rotation of said rod.

10. The module according to claim 7 wherein the drive mechanism comprises a pneumatically or hydraulically operated piston secured about one end of an elongate rod, said retainer member being secured about the opposite end of said elongate rod for the displacement of said sleeve along the longitudinal axis of the composite tubing of said lamp when said piston is activated.

11. The module according to claim 1 additionally comprising a housing for said drive mechanism.

12. The module according to claim 11 wherein said housing, ultraviolet light apparatus, and drive mechanism form a single unit.

13. The module according to claim 12 wherein said housing additionally includes a ballast for powering said ultraviolet light apparatus.

14. The module according to claim 13 wherein said housing additionally includes a switch means for automatically disconnecting power to said lamp when said housing is separated from said confined space.

15. The module according to claim 13 wherein said housing additionally includes an electrically activated, audible and/or visual alarm when said lamp, ballast or drive mechanism ceases to function.

16. An ultraviolet light system for the treatment of air comprising:
    (a) a conduit for the passage of air therethrough;
    (b) an ultraviolet light apparatus comprising an ultraviolet light-emitting lamp that includes at least one composite tubing, said composite tubing comprising:
        (i) a first section for transmitting ultraviolet light in a wavelength range that includes maximum ozone production and maximum germicidal activity;
        (ii) a second section for transmitting ultraviolet light in a wavelength range that includes maximum germicidal activity and excludes the production of ozone; and
        (iii) an annular sleeve, the annulus of said sleeve
            (A) being capable of completely surrounding a portion of the composite tubing of said lamp; and (B) being capable of blocking ultraviolet light in a wavelength range that produces ozone while simultaneously allowing the transmission of ultraviolet light in a wavelength range that produces germicidal activity;

(c) a drive mechanism for the frictionless displacement of said annular sleeve along the longitudinal axis of said composite tubing for controlling the amount of ozone transmitted by said ultraviolet light apparatus within said conduit; and (d) a housing for said drive mechanism, said housing, ultraviolet light apparatus and drive mechanism forming a single unit that is incorporated with said conduit.

17. The system according to claim 16 wherein said lamp comprises two, substantially parallel, tubularly connected segments, the first section of said composite tubing forming a portion of at least one of said segments.

18. The system according to claim 16 wherein said sleeve allows the transmission of ultraviolet light that is inclusive of the wavelength range for producing maximum germicidal activity.

19. The system according to claim 18 wherein said sleeve is constructed of fused quartz.

20. The system according to claim 18 wherein said sleeve is constructed of transparent Teflon.

21. The system according to claim 16 wherein said sleeve has a cylindrical configuration and is of sufficient length to completely surround the first section of the composite tubing of said lamp.

22. The system according to claim 16 wherein said drive mechanism comprises an elongate threaded rod engaged at one end portion thereof with a means for rotating said rod, the threaded portion of said rod being operatively engaged with a correspondingly threaded opening within a retainer member fixed to said sleeve for displacing said sleeve along the longitudinal axis of the composite tubing of said lamp when said rod is rotated.

23. The system according to claim 22 wherein said means for rotating said rod comprises an electric motor.

24. The system according to claim 22 wherein said means for rotating said rod comprises a handle for the manual rotation of said elongate threaded rod.

25. The system according to claim 22 additionally comprising a guide rod detachably fixed to said conduit and communicating with a slidable stabilizer member fixed to said retainer member in parallel relationship with said threaded rod to prevent the transmission of torsional forces to said sleeve by the rotation of said threaded rod.

26. The system according to claim 22 wherein the drive mechanism comprises a pneumatically or hydraulically operated piston secured about one end of an elongate rod, said retainer member being secured to said elongate rod for the displacement of said sleeve along the longitudinal axis of the composite tubing of said lamp when said piston is activated.

27. The system according to claim 16 wherein said housing additionally includes a ballast for powering said ultraviolet light apparatus.

28. The system according to claim 27 wherein said housing additionally includes a switch means for automatically disconnecting power to said lamp when said housing is separated from said conduit.

29. The system according to claim 27 wherein said housing additionally includes an electrically activated, audible and/or visual alarm when said lamp, ballast or drive mechanism ceases to function.

30. An ultraviolet light module for the treatment of air within a confined space comprising:

(a) an ultraviolet light apparatus comprising an ultraviolet light-emitting lamp that includes (i) tubing for transmitting ultraviolet light in a wavelength range that includes maximum ozone production and maximum germicidal activity; and (ii) an annular sleeve, the annulus of said sleeve (A) completely surrounding all or a portion of the tubing of said lamp; and (B) being capable of blocking ultraviolet light in a wavelength range that produces ozone while simultaneously allowing the transmission of ultraviolet light in a wavelength range that produces germicidal activity; and (b) a drive mechanism for the frictionless displacement of said annular sleeve along the longitudinal axis of said tubing for controlling the amount of ozone transmitted by said ultraviolet light apparatus.

31. The module according to claim 30 wherein said lamp comprises two, substantially parallel, tubularly connected segments.

32. The module according to claim 30 wherein said sleeve allows the transmission of ultraviolet light that is inclusive of the wavelength range for producing maximum germicidal activity.

33. The module according to claim 30 wherein said sleeve has a cylindrical configuration and is of sufficient length to completely surround the tubing of said lamp.

34. The module according to claim 30 wherein said sleeve is constructed of fused quartz.

35. The module according to claim 30 wherein said sleeve is constructed of transparent Teflon.

36. The module according to claim 30 wherein said drive mechanism comprises an elongate threaded rod engaged at one end portion thereof with a means for rotating said rod, the opposite end portion of said rod being operatively engaged with a correspondingly threaded opening within a retainer member fixed to said sleeve for displacing said sleeve along the longitudinal axis of the tubing of said lamp when said rod is rotated.

37. The module according to claim 36 wherein said means for rotating said rod comprises an electric motor.

38. The module according to claim 36 wherein said means for rotating said rod comprises a handle for the manual rotation of said rod.

39. The module according to claim 30 wherein the drive mechanism comprises a pneumatically or hydraulically operated piston secured about one end of an elongate rod, said retainer member being secured about the opposite end of said elongate rod for the displacement of said sleeve along the longitudinal axis of the tubing of said lamp when said piston is activated.

40. The module according to claim 30 additionally comprising a housing for said drive mechanism.

41. The module according to claim 40 wherein said housing, ultraviolet light apparatus, and drive mechanism form a single unit.

42. The module according to claim 41 wherein said housing additionally includes a ballast for powering said ultraviolet light apparatus.

43. The module according to claim 42 wherein said housing additionally includes a switch means for automatically disconnecting power to said lamp when said housing is separated from said confined space.

44. The module according to claim 42 wherein said housing additionally includes an electrically activated, audible and/or visual alarm when said lamp, ballast or drive mechanism ceases to function.

* * * * *